(12) United States Patent
Nilsson et al.

(10) Patent No.: US 12,303,365 B2
(45) Date of Patent: May 20, 2025

(54) DISPOSABLE ABSORBENT HYGIENE ARTICLE HAVING A WAIST FRINGE REGION

(71) Applicant: Essity Hygiene and Health Aktiebolag, Gothenburg (SE)

(72) Inventors: Lisa Nilsson, Gothenburg (SE); Yasha Asayesh, Gothenburg (SE)

(73) Assignee: ESSITY HYGIENE AND HEALTH AKTIEBOLAG, Gothenburg (SE)

( * ) Notice: Subject to any disclaimer, the term of this patent is extended or adjusted under 35 U.S.C. 154(b) by 0 days.

(21) Appl. No.: 18/547,474

(22) PCT Filed: Mar. 2, 2021

(86) PCT No.: PCT/SE2021/050178
§ 371 (c)(1),
(2) Date: Aug. 22, 2023

(87) PCT Pub. No.: WO2022/186740
PCT Pub. Date: Sep. 9, 2022

(65) Prior Publication Data
US 2024/0033136 A1 Feb. 1, 2024

(51) Int. Cl.
*A61F 13/49* (2006.01)
(52) U.S. Cl.
CPC .. *A61F 13/49011* (2013.01); *A61F 13/49017* (2013.01)
(58) Field of Classification Search
CPC ........ A61F 13/49; A61F 13/496; A61F 13/64; A61F 13/15; A61F 13/53; A61F 13/51;
(Continued)

(56) References Cited

U.S. PATENT DOCUMENTS 10,632,026 B2    4/2020 Ottery et al.
2002/0151858 A1  10/2002 Karami et al.
(Continued)

FOREIGN PATENT DOCUMENTS

EP    2246020 A1    11/2010
WO    9514453 A2    6/1995
(Continued)

OTHER PUBLICATIONS

International Search Report & Written Opinion for International Application No. PCT/SE2021/050178; International Filing Date: Mar. 2, 2021; Date of Mailing: Nov. 1, 2021; 12 pages.
(Continued)

*Primary Examiner* — Michele Kidwell
(74) *Attorney, Agent, or Firm* — CANTOR COLBURN LLP (57) ABSTRACT

The present disclosure relates to a disposable open-type absorbent hygiene article, comprising an absorbent assembly and an elastic back panel, wherein said elastic back panel comprises a panel material comprising elastic threads extending in said transverse direction (x) and being spaced apart in said longitudinal direction (y), said elastic threads providing elasticity to said elastic back panel, and said elastic back panel comprises no or only disabled elastic threads in a waist fringe region extending over a longitudinal length (Lw) from said second edge of said back panel towards said first edge of said back panel, wherein said length (Lw) is at least 3 mm.

19 Claims, 3 Drawing Sheets

(58) Field of Classification Search
CPC ............... A61F 13/56; A61F 13/49061; A61F 13/49011; A61F 2013/49036; A61F 2013/49026
See application file for complete search history.

(56) References Cited

U.S. PATENT DOCUMENTS

| | | | | |
|---|---|---|---|---|
| 2005/0126689 | A1* | 6/2005 | Thorson | A61F 13/49011 |
| | | | | 156/204 |
| 2006/0036227 | A1* | 2/2006 | Hoshino | A61F 13/49019 |
| | | | | 604/385.3 |
| 2007/0203468 | A1* | 8/2007 | Inoue | A61F 13/84 |
| | | | | 604/378 |
| 2008/0108964 | A1* | 5/2008 | Edwall | A61F 13/496 |
| | | | | 604/385.24 |
| 2008/0161768 | A1* | 7/2008 | Baba | A61F 13/49017 |
| | | | | 604/385.27 |
| 2012/0330264 | A1* | 12/2012 | Lawson | A61F 13/49017 |
| | | | | 604/385.01 |
| 2013/0324956 | A1* | 12/2013 | Zink | A61F 13/15699 |
| | | | | 604/365 |
| 2015/0290048 | A1 | 10/2015 | Sugiyama et al. | |
| 2017/0105884 | A1* | 4/2017 | Wade | A61F 13/49011 |
| 2017/0290716 | A1* | 10/2017 | Morimoto | A61F 13/49011 |

FOREIGN PATENT DOCUMENTS

| | | | | |
|---|---|---|---|---|
| WO | 2011/087503 | * | 7/2011 | A61F 13/15 |
| WO | 2013080782 | A1 | 6/2013 | |
| WO | 2014057974 | A1 | 4/2014 | |

OTHER PUBLICATIONS

European Application No. 21929345.3-1102; Extended European Search Report dated Oct. 7, 2024; 5 pages.

* cited by examiner

DISPOSABLE ABSORBENT HYGIENE ARTICLE HAVING A WAIST FRINGE REGION

CROSS REFERENCE TO RELATED APPLICATIONS

This application is a National Stage Application of PCT/SE2021/050178, filed Mar. 2, 2021, which is incorporated by reference in its entirety herein.

TECHNICAL FIELD

The present disclosure relates to a disposable open-type absorbent hygiene article, such as a diaper or incontinence article.

BACKGROUND

Disposable absorbent hygiene articles, for example in the form of diapers and incontinence garments, are well known. Such articles are used for absorbing, distributing and storing various types of body exudates, for example urine, while providing a high level of comfort and sense of dryness to the wearer during use. A conventional disposable absorbent article is normally designed with an absorbent assembly comprising an absorbent core which is sandwiched between a top sheet and a back sheet.

The absorbent assembly may comprise a first portion and a second portion, defining a longitudinal extension of the article from the first portion to the second portion, and opposing side edges extending from the first portion to the second portion, defining a transverse extension between the side edges.

Some disposable absorbent hygiene articles, for example diapers and incontinence garments, comprise front and/or back side panels which extend beyond the side edges of the absorbent assembly. When the article is in a use position with the absorbent assembly positioned over the crotch of the wearer, the front and/or back side panels are configured to form at least part of a waist opening around the waist of the wearer, and leg openings for the legs of the wearer are formed between the side panels and the absorbent assembly.

An open-type absorbent hygienic article, such as an open-type diaper, is an article which is provided to a user in an open state and which is configured to be closed to form a closed state around the wearer's waist when the article is worn (in the use position). To this end, the front and/or back side panels may be provided with fasteners for closing the article around a wearer when the article is applied. The fasteners may be openable and re-closable to allow for reclosing of the article for example for inspection thereof after some time of use, or for adjustment of the size of the waist opening of the article.

As such, open-type absorbent articles differ from pant-type articles. Pant-type articles are provided to a user in a closed state and are pulled over the legs of the wearer when applied. In such articles, front and back side panels extending from the absorbent assembly are conventionally permanently joined to each other by means of a seam in each side of the article, so as to form a pant-like article with a waist opening and leg openings. A pant-type article may be removed either by pulling it down along the legs of the wearer, or by ripping open the article by destruction of its side seams. Pant-type articles are thus provided in fixed sizes.

WO 95/14453 describes examples of open-type absorbent articles.

There is a continuous need for improvement in open-type absorbent articles as described in the above. Such needs may relate to one or more of needs for improving comfort to the wearer, needs for facilitating production, and needs for enabling efficient use of materials.

It is desired to provide an open-type absorbent hygiene article which may fulfil one or more of the above-mentioned needs.

SUMMARY

Such an article is provided by an article as defined by the appended claim 1.

As such, there is provided a disposable open-type absorbent article having a longitudinal direction and a transverse direction, perpendicular to the longitudinal direction, and comprising an absorbent assembly and an elastic back panel. The absorbent assembly comprises a first portion and a second portion, and opposing side edges extending in the longitudinal direction from the first portion to the second portion.

The elastic back panel extends in the longitudinal direction between a first edge and a second edge, and is permanently joined to the second portion of the absorbent assembly so as to extend beyond the side edges of the absorbent assembly in the transverse direction of the article, so as to form elastic side portions configured to contact and be fastened to the first portion of the absorbent assembly when the absorbent article is worn. The second edge of the elastic back panel forms a continuous waist edge at the back and sides of the wearer when the article is worn, and the first edge of the elastic back panel in the elastic side portions, together with the side edges of the absorbent assembly, form leg openings around the legs of the wearer when the article is worn.

The elastic back panel comprises a panel material comprising elastic threads extending in the transverse direction and being spaced apart from each other in the longitudinal direction, the elastic threads providing elasticity to the elastic back panel. In accordance with the present disclosure, the elastic back panel comprises no or only disabled elastic threads in a waist fringe region extending over a longitudinal length from the second edge of the back panel towards the first edge of the back panel, wherein the length is at least 3 mm.

As such, the waist fringe region will be non-elastic due to the lack of active elastic threads therein. The panel material of the elastic back panel will hence form a soft wrinkled edge in said waist fringe region. This provides for increased comfort to a wearer and for an aesthetically pleasing appearance.

When the article is worn, the elastic back panel extending over the back and sides of the wearer provides for comfort and fit, as the elastic back panel is able to adapt to the wearer's body and movements. In use, the elastic back panel may be repeatedly stretched and contracted, stretching and contracting the elastic threads. The waist fringe region provides for softness at the uppermost end of the waist of the article, diminishing the risk of chafing at the upper edge (the second edge) of the back panel.

The elastic side portions of the elastic back panel extend beyond the side edges of the absorbent assembly, i.e. the elastic side portions of the elastic back panel extend on a respective side of the absorbent assembly.

The second edge of the back panel is to be determined as the outermost portion of the edge of the back panel in a direction away from the absorbent assembly along the longitudinal direction (y). The second edge hence forms the uppermost waist edge of the article when the article is worn. The second edge of the back panel may remain at the same height as seen along the longitudinal direction over a majority of its transverse width. The second edge of the back panel may remain at the same height as seen along the longitudinal direction over at least 75% of its transverse width. Similarly, the waist fringe region may extend over a majority of the transverse width of the back panel. The waist fringe region may extend over at least 75% of the transverse width of the back panel.

The waist fringe region length in a longitudinal direction may be selected to provide the desired softness. For example, the waist fringe region may extend over a longitudinal length from the second edge of the back panel towards the first edge of the back panel being within the range of from 3 to 15 mm. For example, the length may be within the range of from 3 to 10 mm.

At least in the elastic side portions of the elastic back panel, the elastic back panel may comprise no or only disabled elastic threads in a leg fringe region extending over a longitudinal length from the first edge of the back panel in the side panels towards the second edge of the back panel in the side panels, wherein the length is at least 5 mm.

As such, the provision of a leg fringe region may provide for increased comfort and softness as well as an aesthetically pleasing design at the leg openings of the article.

For example, the leg fringe region may extend over a longitudinal length from the first edge of the back panel being within the range of from 5 to 20 mm. For example, the length may be within the range of from 5 to 15 mm.

The leg fringe region may extend along the entire first edge of the elastic back panel. When the leg fringe region extends along the entire first edge of the elastic back panel, this implies that the leg fringe region extends at least in the elastic side portions of the elastic back panel. That the leg fringe region extends along the entire first edge of the elastic back panel may be advantageous considering the manufacture of the article, since it allows for e.g. the elastic threads to be removed or disabled from/in a continuous leg fringe region extending along the first edge of the elastic back panel.

The first edge of the back panel is to be determined as the outermost portion of the edge of the back panel in a direction towards the absorbent assembly along the longitudinal direction. The first edge of the back panel may remain at the same height as seen along the longitudinal direction over a majority of its transverse width. The first edge of the back panel may remain at the same height as seen along the longitudinal direction over at least 75% of its transverse width.

Similarly, the leg fringe region may extend over a majority of the transverse width of the back panel. The leg fringe region may extend over at least 75% of the transverse width of the back panel.

The elastic back panel may for example be arranged on the garment-facing side of the article. To this end, the elastic back panel may be arranged over a garment-facing side of the absorbent assembly, e.g. over the back sheet of the absorbent assembly.

When the elastic back panel is arranged towards the garment-facing side of the article, e.g. over the back sheet of the absorbent assembly, the elastic back panel may nevertheless at least partly face the wearer-facing side of the article, i.e. contact the wearer when the article is worn. For example, at least the elastic side portions of the elastic back panel may be arranged so as to contact the wearer when the article is worn.

The absorbent assembly may extend in the longitudinal direction y between an assembly first edge and an assembly second edge. The assembly first edge is directed towards the same direction as the first portion of the absorbent assembly, hence towards the front portion of the article. The assembly second edge is directed towards the same direction as the second portion of the absorbent assembly, hence towards the back portion of the article.

The permanent attachment of the absorbent assembly to the elastic back panel may be made such that at least a portion of the elastic back panel extends longitudinally beyond the second edge of the absorbent assembly. Thus, a portion of the elastic back panel extending longitudinally beyond the second edge of the absorbent assembly may contact the waist region of a wearer when the article is worn.

In another example, the elastic back panel may be arranged towards the wearer-facing side of the article. In this case, the elastic back panel may be arranged over the topsheet of the absorbent assembly This implies that substantially the entire elastic back panel will contact the wearer when the article is worn.

In all of the above-mentioned options, the article may be configured such that at least the waist fringe region contacts the wearer when the article is worn.

The waist fringe region may extend longitudinally beyond the second edge of the absorbent assembly.

The longitudinal length of the leg fringe region may be greater than the longitudinal length of the waist fringe region. For example, the longitudinal length of the leg fringe region may be at least 2 mm greater than the longitudinal length of the waist fringe region.

The elastic threads may be uniformly spaced from each other, i.e. arranged at the same distance from each other as seen in the longitudinal direction over a major part of the longitudinal extension of the elastic back panel. This enables use of conventional panel materials with elastic threads as starting materials for forming the elastic back panel. Also, this allows for an even elasticity in the back panel outside of the waist fringe region and any leg fringe regions.

The elastic threads may be uniformly spaced from each other in the longitudinal direction over a full longitudinal extension of the elastic back panel apart from in the waist fringe region, and, when there is a leg opening fringe region, preferably apart from in the leg opening fringe region.

Alternatively, the back panel may comprise inelastic and elastic zones, where the elastic zones comprise a plurality of elastic threads. For example, the back panel may comprise two to three zones comprising elastic threads.

The back panel, when in a stretched out condition, may have a transverse extension being at least 150% of the transverse extension of the first portion of the absorbent assembly. For example, at least 180%. Or in another example at least 190%.

Thus, the back panel is intended to extend over the majority of the waist circumference of a user, providing the desired comfort and fit.

With "stretched out condition" is meant a condition in which the elastic threads are stretched out such that the panel material of the elastic back panel reaches its maximum dimension in the transverse direction, but that the panel material is not stretched per se.

The transverse extension of the first portion may be measured at the location were the elastic side portions are to be fastened to the first portion of the absorbent assembly. For example, this may be at the location of a landing zone for fastening elements provided at the side portions.

The transverse extension of the back panel when in a stretched out condition may be within the range of from 150 to 250% of the transverse extension of the first portion of the absorbent assembly. For example, within the range of from 180 to 230%, or in another example within the range of from 190 to 215%.

The transverse extension of the first portion of the absorbent assembly may be in the range 400 to 600 mm. The back panel may have a longitudinal length within the range of from 80 to 150 mm.

In the context of the present disclosure, a longitudinal length is to be understood as the longest length of a specified part or sub-part in the longitudinal direction. Analogously, a transverse width is to be understood as the widest width of specified part or sub-part in the transverse direction.

For the purposes of the present disclosure, and unless otherwise explicitly mentioned, lengths, widths and other dimensions of a disposable absorbent hygiene product are measured with the disposable absorbent hygiene product in a relaxed flattened out state on a flat surface with any contracting elements being deactivated Each of the elastic side portions may carry at least one fastener. The fastener may be configured to fasten the elastic side portion to the first portion of the absorbent assembly.

The fastener may be arranged outside of the waist fringe region. When there is a leg opening fringe region, the fastener may be arranged outside of the leg fringe region.

The fastener may be an openable and reclosable fastener.

The elastic side portions may form tapered ends to contact and be fastened to the first portion of the absorbent assembly when the absorbent article is worn.

In a second aspect, there may be provided a disposable open-type absorbent hygiene article having a longitudinal direction and a transverse direction, perpendicular to the longitudinal direction, and comprising an absorbent assembly and an elastic back panel.

The absorbent assembly comprises a first portion and a second portion, and opposing side edges extending in the longitudinal direction from the first portion to the second portion, the elastic back panel having a first edge and a second edge, and being permanently joined to the second portion of the absorbent assembly so as to extend beyond the side edges of the absorbent assembly in the transverse direction of the article, so as to form elastic side portions configured to contact and be fastened to the first portion of the absorbent assembly when the absorbent article is worn, such that the second edge of the elastic back panel forms a continuous waist edge at the back and sides of the wearer when the article is worn, and such that the first edge of the elastic back panel in the elastic side portions, together with side edges of the absorbent assembly, form leg openings around the legs of the wearer when the article is worn. At least in the elastic side portions of the elastic back panel, the elastic back panel comprises no or only disabled elastic threads in a leg fringe region extending over a longitudinal length from the first edge of the back panel in the side panels towards the second edge of the back panel in the side panels, wherein the length is at least 5 mm. As such, leg fringe regions are provided at least in the portions of the elastic back panel forming the elastic side portions.

As such, in the second aspect, there is provided an article having a leg fringe region, but not necessarily a waist fringe region. Such an article may be combined with all the features and aspects mentioned in the above, and providing similar advantages.

BRIEF DESCRIPTION OF THE DRAWINGS

With reference to the appended drawings, below follows a more detailed description of variants of the open-type absorbent articles cited as examples.

DETAILED DESCRIPTION

Figure 1:
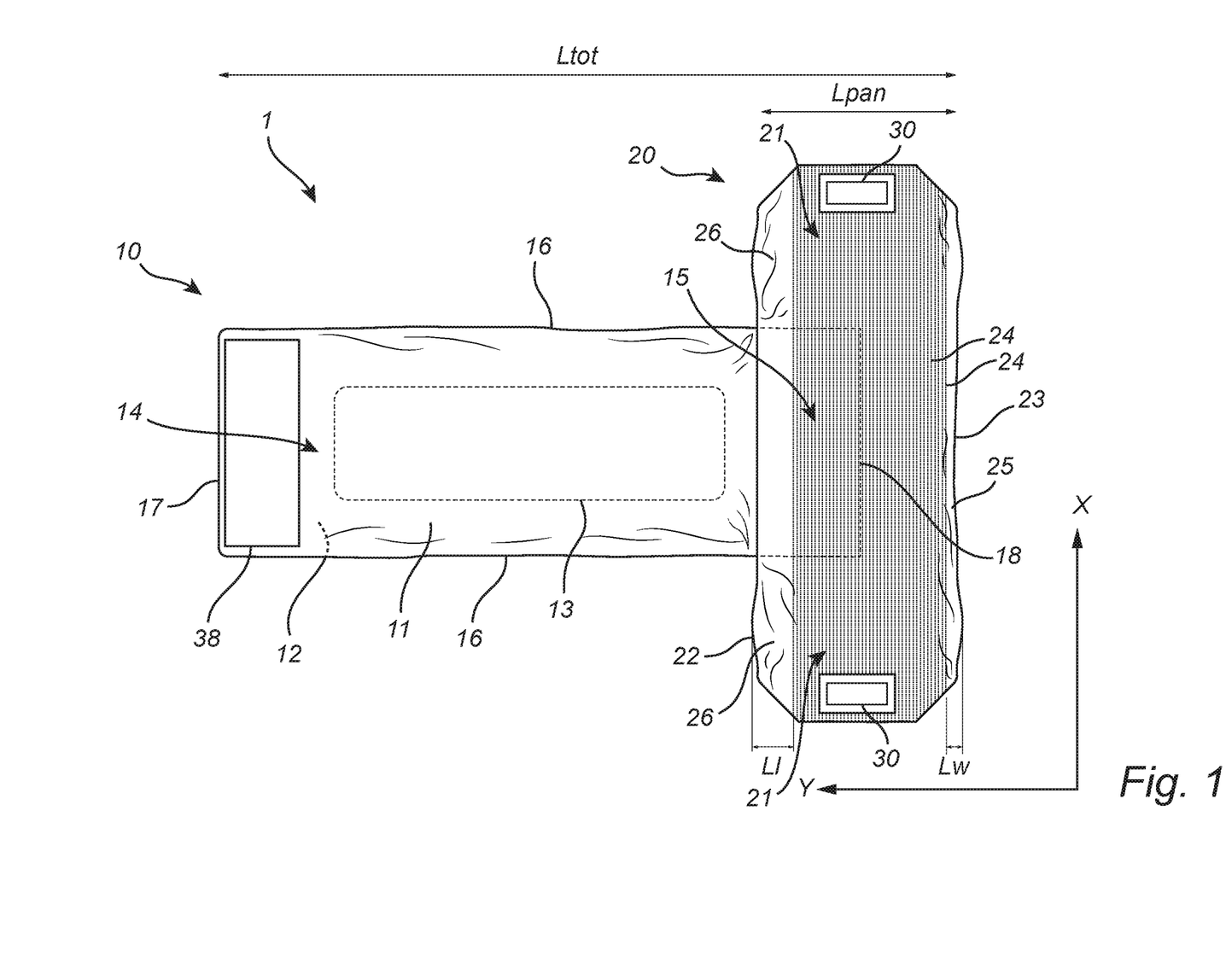
FIG. 1 is a schematic illustration of an open-type article as seen from a garment-facing side.

The following description relates to an absorbent article 1 being a baby diaper. The diaper should be seen as an example of a disposable open-type absorbent article which may comprise an absorbent assembly 10 and elastic side portions 21 such as illustrated in FIG. 1. However, the present disclosure may be implemented in a plurality of different types of disposable open-type absorbent articles such as adult diapers, incontinence garments and the like.

FIG. 1 illustrates a disposable open-type absorbent article 1 having a longitudinal direction y and a transverse direction x, perpendicular to the longitudinal direction y. The article 1 also has a height direction perpendicular to the longitudinal direction y and transverse direction x.

In the context of the present disclosure "disposable" is used in its ordinary sense to mean an article that is disposed or discarded after a limited number of usage events over varying lengths of time, for example, less than 10 events, less than about 5 events, or after 1 event.

Figure 2:
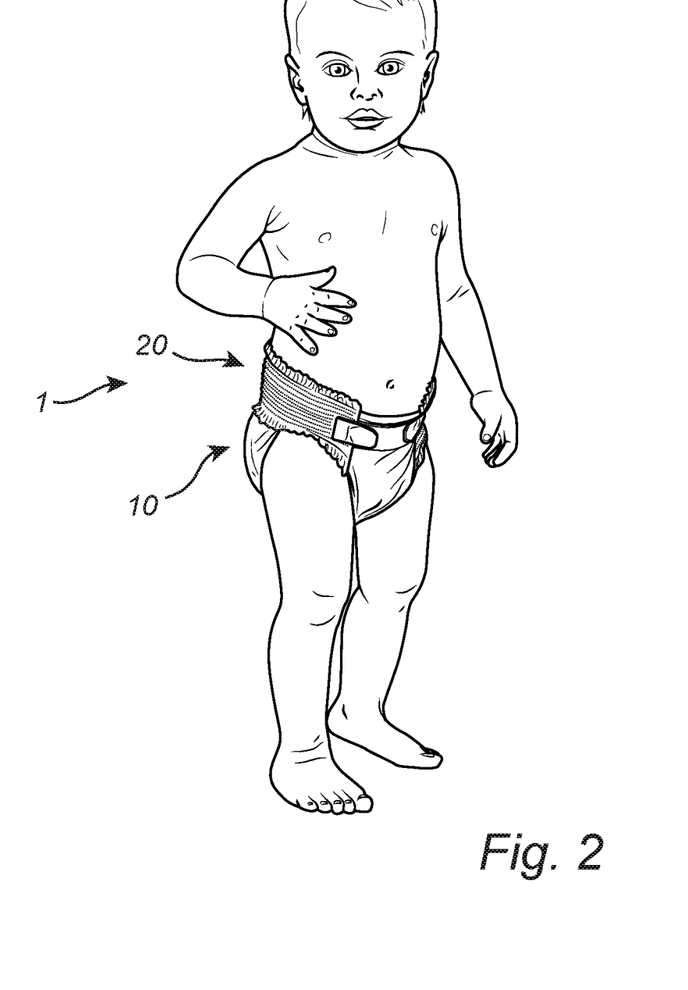
FIG. 2 is an illustration of the article in FIG. 1 when worn.

The article 1 is an open-type absorbent article meaning that it is provided in an open state (as illustrated in FIG. 1) to a user, and is closed to form a waist opening and two leg openings when applied to a wearer (as illustrated in FIG. 2).

The article 1 comprises an absorbent assembly 10, and an elastic back panel 20.

The absorbent assembly 10 has a first portion 14 and a second portion 15 and opposing side edges 16 extending in the longitudinal direction Y from the first portion 14 to the second portion 15. The first portion 14 is intended to be at the front (belly) waist region of the user, and the second portion 15 intended to be in the back region of the user when the article 1 is worn. The absorbent assembly 10 extends longitudinally between an assembly first edge 17 and an assembly second edge 18, wherein the assembly first edge 17 is intended to be directed towards the front of the user, and the assembly second edge 18 is intended to be directed towards the back of the user.

Accordingly, the assembly first edge 17 is directed towards the same direction as the first portion 14 of the absorbent assembly 10, hence towards the front portion of the article 1. The assembly second edge 18 is directed towards the same direction as the second portion 15 of the absorbent assembly 10, hence towards the back portion of the article 1.

The absorbent assembly 10 may comprise a back sheet 11, a top sheet 12, and an absorbent core 13 positioned between the back sheet 11 and top sheet 12.

The back sheet 11 may typically be a liquid impermeable back sheet 11 at the garment facing side of the absorbent assembly 10. Materials suitable as back sheets are commonly known in the art of disposable absorbent hygiene products. The back sheet 11 may preferably be substantially impermeable to liquids such as urine. The back sheet may be breathable, i.e. gas permeable, implying that air and other gases may pass through the back sheet 11, while being substantially impermeable to liquids. For the purposes of the present disclosure, any material commonly known for use as back sheet materials may be included in the backsheet, including but not limited to polymeric films, hydrophobized nonwoven materials, fluid impermeable foams and fluid impermeable laminates. The back sheet may comprise one or more layers of material.

The top sheet 12 may typically be a liquid permeable top sheet 12 at the body facing side of the absorbent assembly 10. Materials suitable for top sheet 12 are commonly known in the art of disposable absorbent hygiene products, and for the purposes of the present disclosure any material commonly known for use as top sheet materials may be used, including, but not limited to woven materials, non-woven materials, perforated polymeric films, open cell foams, or combinations or laminates of these materials. The top sheet 12 may suitably be sufficiently fluid permeable to allow discharged body fluids such as urine to penetrate through the thickness of the top sheet 12. Also, the top sheet 12 is suitably manufactured from a material which is compliant and soft-feeling to the skin of the wearer.

The absorbent core 13 may comprise any suitable absorbent material, for example cellulosic fibers and/or super absorbent polymers.

In the disposable absorbent article 1, the top sheet 12 and the back sheet 11 may extend outside the outer contour of the absorbent core 13 and be joined together outside the absorbent core 13 contour using methods commonly known in the art such as gluing or welding by means of heat or ultrasound.

Further, the absorbent assembly 10 may comprise one or more additional layers such as an acquisition layer or a distribution layer.

The absorbent assembly 10 may further display any additional features as used in the art, such as for example raised elastic members, commonly known as standing gathers. The absorbent assembly 10 may also be provided with a wetness indicator.

The article 1 of FIG. 1 comprises an elastic belt panel 20 being permanently attached to the second portion 15 of the absorbent assembly 10. The elastic belt panel 20 extends in the longitudinal direction Y between a first edge 22 and a second edge 23. The elastic belt panel 20 extends beyond the side edges 16 of the absorbent assembly 10 in the transverse direction X of the article 1, so as to form an elastic side portion 21 extending beyond each of the side edges 16 of the absorbent assembly 10 in the transverse direction X of the article 1. The side portions 21 are configured to contact and be fastened to the first portion 14 of the absorbent assembly 10 when the absorbent article 1 is worn.

When worn, it is hence intended that the first portion 14 of the absorbent article 1 will be directed towards the front of the wearer, with the top sheet 12 facing the wearer. As may be seen in FIG. 2, when worn, the second edge 23 of the elastic back panel 20 forms a continuous waist edge at the back and sides of the article 1. The first edge 22 of the elastic back panel 20 in the elastic side portions 21, together with side edges 16 of the absorbent assembly 10, form leg openings around the legs of the wearer.

Turning back to FIG. 1, in the article illustrated therein, the elastic back panel 20 comprises a panel material comprising elastic threads 24 extending in the transverse direction x and being spaced apart in the longitudinal direction y.

The elastic threads 24 provides elasticity to the elastic back panel 20, such that it may be stretched in the transverse direction x.

The back panel 20 may be made by any suitable elastic material comprising elastic threads. For example, the back panel 20 may comprise a nonwoven material, or a laminate nonwoven material comprising elastic threads. For example, the back panel 20 may comprise elastic threads arranged between two plies of nonwoven material. The back panel material may be selected to be a material being satisfactory when it comes to softness when the elasticity of the elastic threads is removed.

As further illustrated in FIG. 1, the elastic back panel 20 comprises no elastic threads 24 in a waist fringe region 25 extending over a longitudinal length Lw from the second edge 23 of the back panel 20 towards the first edge 22 of the back panel 20, wherein the length Lw is at least 3 mm. As a result, the waist fringe region 25 may form folds or creases at the waist of the article 1 when in a closed condition. The waist fringe region 25 may hence form a soft edge providing increased comfort to the wearer of the article 1.

In a non-illustrated variant, the elastic back panel 20 may comprise only disabled elastic threads 24 in the waist fringe region 25. The elastic threads 24 may be disabled e.g. by being cut at one or more locations, such that the waist fringe region 25 is not subject to stress from the elastic threads 24.

The waist fringe region 25 extending over a longitudinal length Lw from the second edge 23 of the back panel 20 towards the first edge 22 of the back panel 20, where the length Lw is at least 3 mm may display a suitable length to provide the desired comfortable waist fringe region. The length Lw may be less than 15 mm, for example less than 10 mm.

As illustrated in FIG. 1, at least in the elastic side portions 21 of the elastic back panel 20, the elastic back panel 20 may comprise no or only disabled elastic threads 24 also in a leg fringe region 26 extending over a longitudinal length Ll from the first edge 22 of the back panel 20 in the side panels 21 towards the second edge 23 of the back panel 20 in the side panels 21. Thus, a leg fringe region providing increased comfort to a user may be provided also at the leg openings of the article 1 when worn.

The leg fringe region 26 extending over a longitudinal length Ll from the first edge 22 of the back panel 20 in the side panels 21 towards the second edge 23 of the back panel 20 in the side panels 21, wherein the length Ll is at least 5 mm. This may be suitable to form a comfortable leg fringe at the leg opening. The length Ll may 20 mm or less, such as 15 mm or less.

As in the illustrated article 1, the leg fringe region 26 may extend along the entire first edge 22 of the elastic back panel 20. This may provide for simplified construction of the article 1 since it is immediately ensured that the entire elastic side panels 21 will indeed be provided with leg fringe regions 26.

However, other variants are conceivable wherein the leg fringe region 26 extend only along the portions of the elastic back panel 20 which form the elastic side portions 21.

In some variants, and as illustrated in FIG. 1, the longitudinal length Ll of the leg fringe region 26 is greater than the longitudinal length Lw of the waist fringe region 25. Accordingly, the leg fringe region 26 and the waist fringe region 25 may be adapted to the different types of movement of the wearer occurring at the leg opening versus the waist opening.

By virtue of the elastic back panel 20 forming the elastic side portions 21, which are fastened towards the first portion 14 of the absorbent assembly 10 when worn, the elastic side portions 21 may extend continuously over the leg openings which are formed when the article 1 is worn. Accordingly, the side portions 21 are able to adjust to the wearer's movements during use, and seams or the like may be avoided in the regions of the leg openings. This contributes to the comfort experienced by the wearer.

When the article 1 is in a closed condition, each elastic side portion 21 may extend from the second portion 15 to the first portion 14 of the absorbent assembly 10, and the leg opening be formed by the longitudinal edge 16 of the absorbent assembly 10 and the side portion 21.

As in the illustrated example, the elastic side portions 21 may form tapered transverse ends 40 to contact and be fastened to said first portion 14 of said absorbent assembly 10 when said absorbent article 1 is worn.

In some variants, and as illustrated in FIG. 1, the elastic back panel 20 may be provided on the garment facing side of the absorbent assembly 10, i.e. so as to partly cover the back sheet 11. The second edge 18 of the absorbent assembly 10 may be arranged at a distance from the second edge 23 of the back panel 20 such that at least the waist fringe region Lw contacts the wearer. I.e. at least in the waist fringe region Lw, one side of the back panel 20 forms an outer surface of the article 1 towards the garment-facing side thereof, and another side of the back panel 20 forms an inner surface of the article 1 towards the body-facing side thereof.

In a non-illustrated variant, the elastic back panel 20 may be provided on the body facing side of the absorbent assembly 10, i.e. so as to partly cover the top sheet 12. In this case, substantially the entire elastic back panel 20 may contact the wearer when the article is worn.

In another non-illustrated variant, the first edge 22 of the elastic back panel 20 may be permanently attached to the second edge 18 of the absorbent assembly 10. In this case, substantially the entire body facing side of the elastic back panel 20 will contact the wearer and substantially the entire garment facing side of the elastic back panel 20 will contact the garment when the article 1 is worn.

In all of the variants mentioned in the above, the elastic side portions 21 will contact the wearer when the article 1 is worn. Hence, a first side of the elastic side portions 21 may form an inner side of the article 1 towards the body facing side and a second side of the elastic side portions 21 may form an outer side of the article towards the garment facing side. Also, at least the leg fringe regions 26 contact the wearer when the article 1 is worn.

However, it will be understood that the outermost transverse portions of the elastic side portions 21, such as the tapered ends 40 in the illustrated variant, will not contact the wearer when the article is worn, since the outermost transverse portions will be attached to the backsheet 11 of the first portion 14 of the absorbent assembly 10 for closing the article 1.

The back panel 20 may, when in a stretched out condition, have a transverse extension being at least 150% of the transverse extension of the first portion 14 of the absorbent assembly 10. With "a stretched out condition" is meant herein that the back panel 20 is stretched such that the panel material carrying the elastic threads is fully expanded, but not stretched per se. The transverse extension of the back panel 20 in a stretched out condition hence corresponds to the transverse extension of the panel material.

With the transverse extension of the back panel being at least 150% of the transverse extension of the first portion 14 of the absorbent assembly, the back panel 20 may form well over 50% of the waist circumference of the diaper.

The transverse extension of the back panel may be at least 180% of the transverse extension of the first portion 14 of the absorbent assembly. For example, it may be at least 190%.

As illustrated in FIG. 1, each of the elastic side portions 21 may carry at least one fastener 30. The fastener 30 may be arranged outside of the waist fringe region 25, and, when a leg opening fringe region is present, also outside of the leg opening fringe region 26. Accordingly, the fastener 30 will not interfere with the comfort and aesthetical effect provided by the waist fringe region 25 and/or the leg fringe regions 26.

The fastener 30 may be configured to be fastened to a corresponding landing zone 38 arranged at the first portion 14 of the absorbent article.

The fastener 30 may comprise a fastening element configured to accomplish the fastening of the elastic side portion 21 to the first portion 14 of the absorbent assembly 10, for example to a landing zone 38 thereof. The fastening element may comprise e.g. an adhesive, tape or a hook/loop or hook/hook material. The fastening element may form a reclosable fastening element, allowing for the article 1 to be closed to a closed state and then opened to assume an open state several times. This may facilitate for e.g. a caretaker inspecting whether the article is used or not.

The landing zone 38 on the first portion 14 of the absorbent assembly 1 may for example have an extension along the transverse direction X allowing for adjusting the fastening of the fastener 30 to the needs of the wearer. Alternatively, the fastener 30 may be attached by fastening the fastening element immediately onto the topsheet 12 of the absorbent assembly 1.

The possibility of adjusting the location of the fastening element on the first portion 14 when the article 1 is closed allows for adjustment of the size of the waist opening to the wearer, and hence contributes to increased comfort.

Turning back to the description of the elastic back panel 20, as illustrated in FIG. 1, the elastic threads 24 may be substantially uniformly spaced in the longitudinal direction over a major part of the longitudinal extension of the elastic back panel 20.

As illustrated in FIG. 1, the elastic threads 24 may be substantially uniformly spaced in the longitudinal direction Y over a full longitudinal extension of the elastic back panel 20 apart from in the waist fringe region 25 and in the leg opening fringe region 26.

This provides for the elastic back panel 20 having an even elasticity apart from in any fringe regions 25, 26, which are to be non-elastic.

Further, the option enables easy manufacture of the elastic back panel 20 from an elastic material comprising elastic threads as will now be described in relation to FIGS. 3a and 3b.

Figure 3A:
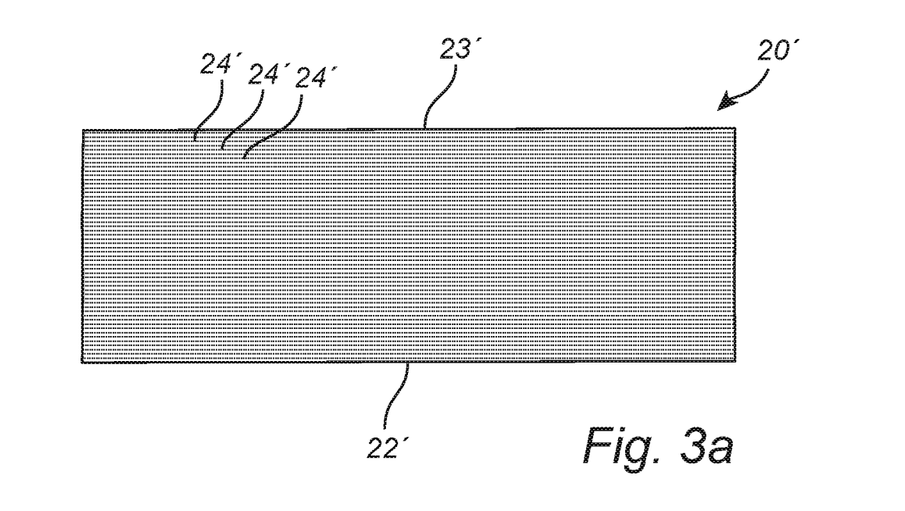
FIG. 3a is a schematic illustration of a piece of elastic material to form an elastic back panel in an article as exemplified in FIG. 1.
Figure 3B:
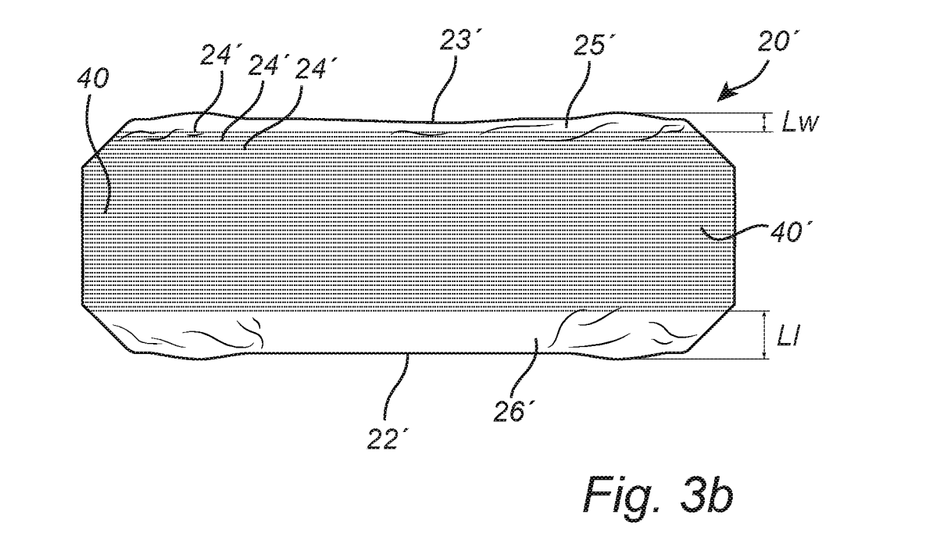
FIG. 3b is a schematic illustration of the piece of elastic material of FIG. 3a when adapted to form an elastic back panel in an article as exemplified in FIG. 1.

FIG. 3a illustrate a piece of starting material 20' to eventually form an elastic side panel 20 in an absorbent article 1. The piece of starting material 20' may be a conventional elastic panel material comprising a panel material provided with elastic threads 24'. The piece may initially be cut to form a rectangle having a length and width suitable for the elastic side panel. The piece 20' extends in a longitudinal direction between a first edge 22' and a second edge 23'. The elastic threads 24' extend in a transverse direction, and, in this example, the elastic threads 24' are uniformly spaced over the longitudinal length of the piece 20'. To form an elastic back panel piece suitable for forming a back panel 20 of an article as described in the above, transverse, the elastic threads 24' may be removed or disabled in a waist fringe region 25' and/or a leg fringe region 26' of the starting material 20'. Hence, a convenient way of forming the waist fringe region 25' and/or the leg fringe regions 26' is to allow said region(s) to extend over the full length of the first and/or second edges 22', 23'. Also, as illustrated in FIG. 3b, the corners of the rectangle starting piece of FIG. 3a may be cut to form tapered outer transverse ends 40' of the starting material 20'. The taper may be made to facilitate attachment of the transverse ends 40' which will form the outermost transversal ends of the elastic side portions 21 in the article 1, to the front portion 14 of the absorbent assembly 10.

In this manner, the piece of starting material 20' may be simply and efficiently formed to be ready to be attached to the absorbent assembly 10 to form the absorbent article 1.

In other, non-illustrated variants the elastic side panel 20 may comprise elastic and inelastic zones, wherein a plurality of elastic threads 24 are arranged in each elastic zone. For example, the elastic side panel 20 may comprise two or more elastic zones, such as two or three elastic zones.

In view of the above-mentioned description of an exemplary absorbent article, it will be understood that many variants and options are available within the scope of the present disclosure.

The invention claimed is:

1. A disposable open-type absorbent hygiene article having a longitudinal direction (y) and a transverse direction (x), perpendicular to said longitudinal direction (y), and comprising:
an absorbent assembly; and
an elastic back panel,
wherein said absorbent assembly comprises a first portion, a second portion, and opposing side edges extending in said longitudinal direction (y) from said first portion to said second portion,
wherein said elastic back panel extends in said longitudinal direction (y) between a first edge and a second edge,
wherein the elastic back panel is permanently joined to said second portion of said absorbent assembly so as to extend beyond said side edges of said absorbent assembly in said transverse direction (x) of said article, so as to form elastic side portions configured to contact and be fastened to said first portion of said absorbent assembly when said absorbent article is worn,
wherein said second edge of said elastic back panel forms a continuous waist edge at the back and sides of the wearer when said article is worn, and
wherein said first edge of said elastic back panel in said elastic side portions, together with side edges of said absorbent assembly, form leg openings around the legs of the wearer when said article is worn,
wherein said elastic back panel comprises a panel material comprising elastic threads extending in said transverse direction (x) and being spaced apart from each other in said longitudinal direction (y),
wherein said elastic threads provide elasticity to said elastic back panel,
wherein said elastic back panel comprises no or only disabled elastic threads in a waist fringe region extending over a longitudinal length (Lw) from said second edge of said back panel towards said first edge of said back panel,
wherein the waist fringe region extends continuously between terminal ends of the elastic back panel in the transverse direction (x),
wherein said length (Lw) is at least 3 mm, and
wherein each of said elastic side portions carries at least one fastener that is openable and reclosable arranged outside of said waist fringe region with no fastener disposed at the waist fringe region.

2. The article according to claim 1, wherein said length (Lw) of the waist fringe region is in the range of from 3 to 15 mm.

3. The article according to claim 2, wherein said length (Lw) of the waist fringe region is within the range of from 3 to 10 mm.

4. The article according to claim 1,
wherein, at least in said elastic side portions of said elastic back panel, said elastic back panel comprises no or only disabled elastic threads in a leg fringe region extending over a longitudinal length (Ll) from said first edge of said back panel in said side panels towards said second edge of said back panel in said side panels,
wherein the leg fringe region extends from terminal ends of the elastic back panel in the transverse direction,
wherein said length (Ll) is at least 5 mm.

5. The article according to claim 4, wherein said length (Ll) of said leg fringe region is within the range of from 5 to 20 mm.

6. The article according to claim 5, wherein said length (Ll) of said leg fringe region is within the range of from 5 to 15 mm.

7. The article according to claim 4, wherein said leg fringe region extends along the entire first edge of said elastic back panel.

8. The article according to claim 4, wherein said longitudinal length (Ll) of the leg fringe region is greater than said longitudinal length (Lw) of the waist fringe region.

9. The article according to claim 1, wherein said elastic threads are uniformly spaced from each other in said longitudinal direction over a major part of a longitudinal extension of said elastic back panel.

10. The article according to claim 1, wherein said back panel, when in a stretched out condition, has a transverse extension being at least 150% of the transverse extension of said first portion of said absorbent assembly.

11. The article according to claim 10, wherein said transverse extension of said back panel when in a stretched out condition is within the range of from 150 to 250% of said transverse extension of said first portion of said absorbent assembly.

12. The article according to claim 11, wherein said transverse extension of said back panel (20) when in a stretched out condition is within the range of from 180 to 230% of said transverse extension of said first portion (14) of said absorbent assembly (10).

13. The article according to claim 12, wherein said transverse extension of said back panel when in a stretched out condition is within the range of from 190 to 215% of said transverse extension of said first portion of said absorbent assembly.

14. The article according to claim 1, wherein said elastic side portions form tapered ends as seen in a transverse direction (x) to contact and be fastened to said first portion of said absorbent assembly when said absorbent article is worn.

15. The article according to claim 1, wherein said elastic threads are uniformly spaced from each other in said longitudinal direction over a full longitudinal extension of said elastic back panel apart from in said waist fringe region.

16. The article according to claim 1, wherein a longitudinal length of a portion of the elastic back panel having the elastic threads is greater than the longitudinal length (Lw) of the waist fringe region.

17. The article according to claim 4, wherein a longitudinal length of a portion of the elastic back panel having the elastic threads is greater than the longitudinal length (Ll) of the leg fringe region.

18. The article according to claim 4, wherein the longitudinal length (Ll) of the leg fringe region is greater than the longitudinal length (Lw) of the waist fringe region.

19. The article according to claim 1, wherein the elastic back panel extends beyond an entirety of said absorbent assembly in said transverse direction (x) of said article.

* * * * *